United States Patent
Kurokawa

[11] Patent Number: 5,317,164
[45] Date of Patent: May 31, 1994

[54] RADIOTHERAPY DEVICE

[75] Inventor: Masaaki Kurokawa, Amagasaki, Japan

[73] Assignee: Mitsubishi Denki Kabushiki Kaisha, Tokyo, Japan

[21] Appl. No.: 985,920

[22] Filed: Dec. 4, 1992

[30] Foreign Application Priority Data

Jun. 12, 1991 [JP] Japan ................................. 3-323106

[51] Int. Cl.$^5$ .............................................. G12G 5/00
[52] U.S. Cl. .................................. 250/492.3; 250/397
[58] Field of Search ................. 250/492.3, 397, 492.1, 250/396 R; 378/10, 137, 138, 113

[56] References Cited

U.S. PATENT DOCUMENTS 2,018,599 10/1935 Brasch ............................. 250/492.3
5,224,137 6/1993 Blomgren .......................... 378/10

FOREIGN PATENT DOCUMENTS 44-19999 8/1969 Japan.

OTHER PUBLICATIONS

H. Tsujii et al., "Clinical Results of the FIF Irradiation in Esophageal Carcinoma", Hokkaido Univ. School of Medicine, Suppl. 3, 1986.

Primary Examiner—Paul M. Dzierzynski
Assistant Examiner—Kiet T. Nguyen
Attorney, Agent, or Firm—Rothwell, Figg, Ernst & Kurz

[57] ABSTRACT

A radiotherapy device includes: a linac 1 for generating an electron beam 9, and a thin guide tube 2 for guiding the electron beam from the linac 1 to the affected part 7 within the body of the patient 6. The orbit of the electron beam 9 is controlled by means of the feedback circuit 8 in response to the output of the deviation detector 6 which detects the leakage of the electron beam outside of the guide tube 2. A high-level dosage can be accomplished without incurring danger of radiation exposure on the operator.

7 Claims, 2 Drawing Sheets

RADIOTHERAPY DEVICE

BACKGROUND OF THE INVENTION

This invention relates to radiotherapy devices for treating patients by means of radiation, and more particularly to radiotherapy devices with enhanced dosage concentration upon the affected parts of the body, by which the exposure of operators to the radiation can effectively be prevented.

In accordance with the operation principles, the conventional radiotherapy devices may be classified into two categories: the external irradiation type and the internal irradiation type. The external irradiation type devices include: medical linacs (linear accelerators), 60° C. (cobalt 60) devices, microtrons, and particle beam therapeutic devices. The internal irradiation type devices include those by which the radiation source is encapsulated within a needle, a pin, or a ribbon.

In the case of the external irradiation type devices, the X-ray, the γ-ray, or the electron beam or other particle beams (such as the proton beam and the neutron beam) are irradiated upon the affected part to give the radiation damage thereon so as to treat it. Among them, the proton beam device exhibits relative superiority with respect to the concentration of the radiation at the affected part. In the case of the linac, the electron beam energy level is generally from 4 MeV to 20 MeV, and the range of penetration within the body is from about 1 centimeters to 10 centimeters. In the case of the internal irradiation type, the radiation source such as 226 Ra (radium 226) is sealed within a needle, etc., and is inserted into the affected part of the body of the patient. Thus, these type of devices exhibit superior concentration to the affected part. The usual radiation species include α-rays, β-rays, and γ-rays.

The conventional radiotherapy devices, however, have the following disadvantage. In the case of the external irradiation type devices such as the medical linacs, 60° C. (cobalt 60) devices, and microtrons, the concentration of the dosage upon the affected part is often insufficient. Further, in the case of the therapeutic devices using particle beams, the buildings for accommodating the accelerators, etc., may become extremely expensive. Thus, as shown in Japanese Utility Model Publication (Kokoku) No. 44-19999, for example, the device can hardly be used for everyday therapeutic purposes.

In the case of the internal irradiation type devices, on the other hand, the operator may be exposed to radiation upon insertion of the radiation source into the body of the patient. Further, the attenuation of radiation is rapid and it is difficult to obtain a high dosage level. Furthermore, the maintenance of the radiation source incurs trouble. For the purpose of effecting an appropriate therapy suited to the patient's conditions, a good number of radiation source species is necessary.

SUMMARY OF THE INVENTION

It is therefore an object of this invention to provide a radiotherapy device with enhanced dosage concentration upon the affected part by which the operator is under no danger of exposure to radiation and a high dosage level appropriate for treating the patient can be obtained, and which can be installed inexpensively at about the cost of the medical linacs.

The above object is accomplished in accordance with the principle of this invention by a radiotherapy device which comprises: radiation generation means for generating an electron beam; a guide tube of a small diameter attached at one end thereof to the radiation generation means, wherein the guide tube is adapted to be inserted at another end thereof into a body of a patient, the guide tube guiding the electron beam from the radiation generation means to the body of the patient; and electron beam convergence means disposed along the guide tube, for converging the electron beam into a thin beam directed to an affected part of the body of the patient.

Preferably the radiotherapy device further includes: deviation detector means for detecting a deviation of the electron beam from a center of the guide tube; and feedback control means coupled to the deviation detector means, for controlling the electron beam convergence means to adjust an orbit of the electron beam along a central axis of the guide tube in response to an output of the deviation detector means. Further, it is preferred that the electron beam convergence means includes a quadrupole magnet assembly or a quadripolar coil assembly. The electron beam convergence means is preferred to include a steering coil assembly, disposed near the quadrupole magnet or coil assembly, for adjusting the direction of the electron beam. Still further, the radiotherapy device may comprise rotation mechanisms for changing an incident angle of the electron beam into the body of the patient. The guide tube may include a joint at which the guide tube is deflectable, the electron beam convergence means including a dipolar coil assembly for deflecting the electron beam at the joint such that an orbit of the electron beam is aligned along a central axis of the guide tube.

BRIEF DESCRIPTION OF THE DRAWINGS

The features which are believed to be characteristic of this invention are set forth with particularity in the appended claims. The structure and method of operation of this invention itself, however, will be best understood from the following detailed description, taken in conjunction with the accompanying drawings, in which:

In the drawings, like reference numerals represent like or corresponding parts or portions.

DETAILED DESCRIPTION OF THE PREFERRED EMBODIMENTS

Referring now to the accompanying drawings, the preferred embodiments of this invention are described.

Figure 1:
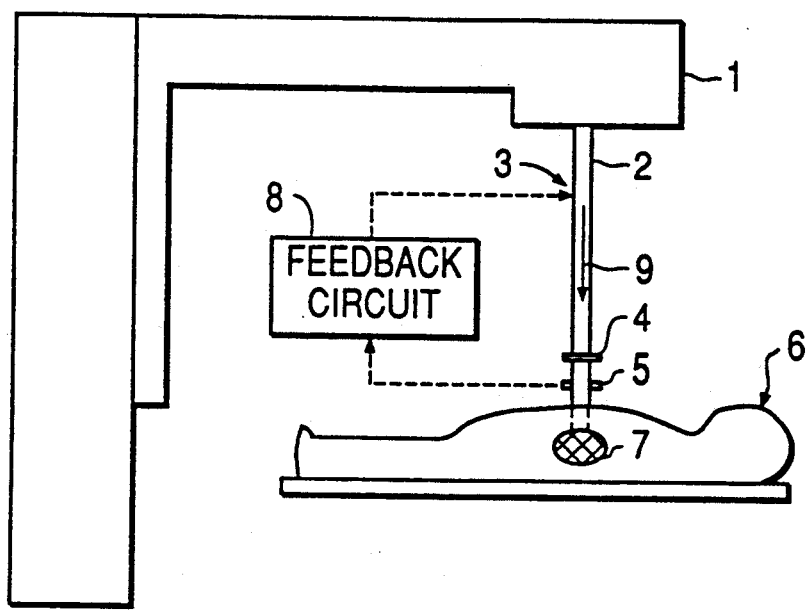
FIG. 1 is a diagrammatic side view of a radiotherapy device according to this invention.

FIG. 1 is a diagrammatic side view of a radiotherapy device according to this invention.

A linac 1 constitutes the radiation generation source for generating the electron beam. A guide tube 2 of about 10 millimeters in diameter extends downward from the linac 1 to the affected part 7 within the body of the patient 6, to guide the electron beam generated by the linac 1. An electron beam convergence means 3, described in detail below, is disposed along the guide tube 2 to prevent the divergence of the electron beam. The end portion of the guide tube 2 inserted into the body of the patient 6 can be detached at an attachment-/detachment mechanism 4. The deviation detector 5 disposed at the end portion of the guide tube 2 detects the deviation of the orbit of the electron beam from the central axis of the guide tube 2.

The electron beam generated by the linac 1 is irradiated upon the affected part 7 through the guide tube 2. For easier insertion into the body of the patient 6, the diameter of the guide tube 2 is small. Thus, the electron beam 9 is converged by the electron beam convergence means 3 to form a thin beam. The deviation detector 5 detects the leakage of the radiation through the wall of the guide tube 2. The leakage of the electron beam at a side of the guide tube 2 implies a deviation of the electron beam to that side. The detection signal of the deviation detector 5 is supplied to the feedback circuit 8, which outputs the feedback signal to the electron beam convergence means 3. On the basis of the feedback signal from the feedback circuit 8, the electron beam convergence means 3 controls the orbit of the electron beam to the center of the guide tube 2. The end portion of the guide tube 2 which is inserted into the body of the patient is detached from the main portion and sterilized before the radiotherapy.

Figure 2A:
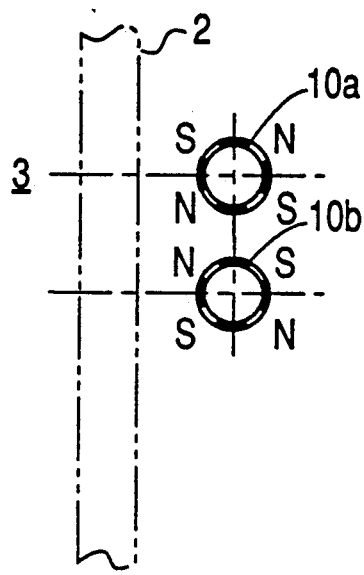
FIG. 2a shows horizontal sections of the quadrupole magnets constituting the primary portion of the electron beam convergence means according to an embodiment of this invention.

Next, the electron beam convergence means 3 is described in detail. FIG. 2a shows horizontal sections of the quadrupole magnets constituting the primary portion of the electron beam convergence means according to an embodiment of this invention. A pair of quadrupole magnet units 10a and 10b are disposed upon the outside wall of the guide tube 2 in complementary polarity, i.e., the units 10a and 10b are disposed such that the north poles of the upper quadrupole magnet 10a are aligned with the south poles of lower quadrupole magnet 10b. Each of the units 10a and 10b include four thin pieces of magnet which are magnetized in the radial direction of the guide tube 2 to exhibit the north and south poles at the interior surface thereof as indicated by the letters N and S in the figure. Preferably, the pieces are made of a strong magnetic material, such as neodium or samarium-cobalt, to reduce the size thereof. Further, by arranging a plurality of quadrupole magnet assemblies, each consisting of the pair 10a and 10b as shown in FIG. 2a, along the guide tube 2, the sufficient convergence of the electron beam can be obtained without increasing the diameter of the guide tube 2.

Figure 2B:
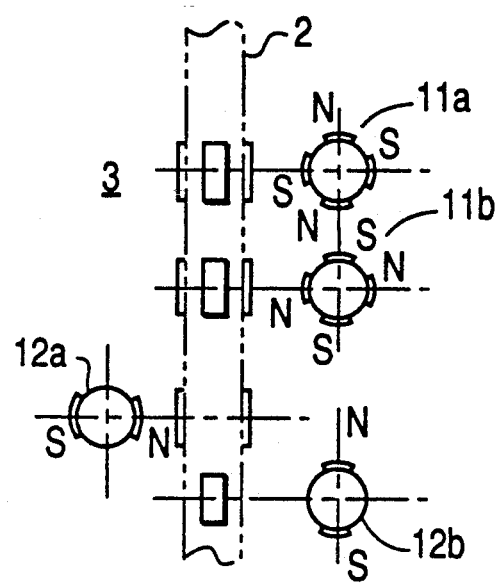
FIG. 2b shows sectional views of the coil units constituting the electron beam convergence means according to an embodiment of this invention.

FIG. 2b shows sectional views of the coil units constituting the electron beam convergence means according to an embodiment of this invention. The same convergence function for the electron beam can be obtained by a pair of coil units 11a and 11b aligned in complementary polarity. Each unit 11a and 11b include four coils having axes extending in the radial direction of the guide tube 2. The coils exhibit north and south poles N and S at the interior side, as indicated in the figure. The intensity of convergence of the electron beam 9 can be controlled by adjusting the levels of the excitation currents supplied to the coils. Preferably, each coil of the coil units 11a and 11b is made of a thin plate-shaped coil. If the coils are made of ribbons of a material exhibiting high-temperature superconductivity, the thickness of the coils can be reduced to an almost negligibly small dimension. The quadrupole coil assemblies, each consisting of the pair of coil units 11a and 11b may be repeated along the length of the guide tube 2.

The quadrupole magnet units 10a and 10b of FIG. 2a, or the quadrupole coil units 11a and 11b, or the combination thereof was used in combination with the steering coil units 12a and 12b. The upper and the lower steering coil units 12a and 12b exhibiting the north and south poles N and S at the interior as shown in the figure are arranged in a complementary manner, such that the magnetic field generated by the two units 12a and 12b are at right angles to each other. The axis of each coil extend in the radial direction of the guide tube 2. By controlling the current levels supplied to the coil units, the deflection of the electron beam within the guide tube 2 can be adjusted.

Figure 2C:
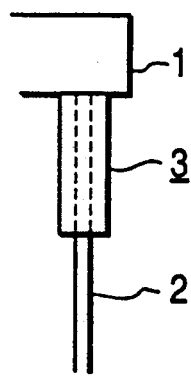
FIG. 2c is a side view of the electron beam convergence means assembly attached to the guide tube according to an embodiment of this invention.

FIG. 2c is a side view of the electron beam convergence means assembly attached to the guide tube according to an embodiment of this invention. by adopting a structure by which the coil or the magnet assembly constituting the electron beam convergence means 3 is attached to the outside wall of the guide tube 2, the assembly of the guide tube 2 can be simplified and the manufacture thereof can be facilitated. The quadrupole magnet units 10a and 10b, the quadrupole coil units 11a and 11b, and the steering coil units 12a and 12b may be disposed only near the end portion of the guide tube 2.

Figure 3:
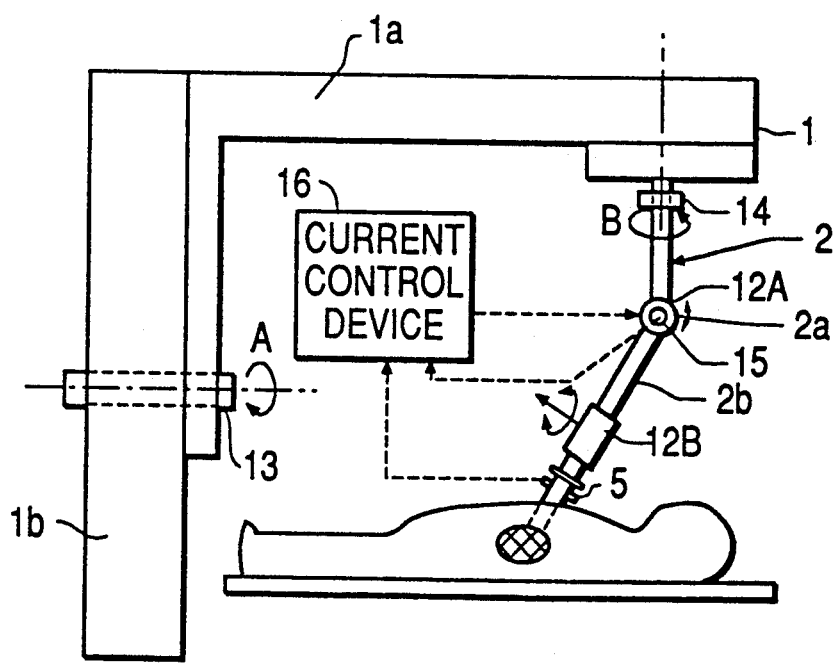
FIG. 3 is a diagrammatic side view of another radiotherapy device according to this invention by which the incident angle of the electron beam can be changed arbitrarily.

In the case of the embodiment of FIG. 1, the incident angle of the electron beam is fixed. FIG. 3 is a diagrammatic side view of another radiotherapy device according to this invention by which the incident angle of the electron beam can be changed arbitrarily. The arm 1a accommodating the linac 1 at the end thereof is rotatably supported on the support frame 1b by means of a rotation mechanism 13. The arm 1a is rotatable round the axis of the rotation mechanism 13. Further, the guide tube 2 is rotatably mounted to the linac 1 by means of the rotation mechanism 14. The guide tube 2 is thus rotatable around the axis thereof. Furthermore, the guide tube 2 includes a joint 2a such that the lower portion 2b thereof is rotatable around the horizontally extending axis of the joint perpendicular to the surface of the drawing. Thus, the incident angle of the electron beam with respect to the patient can be varied arbitrarily.

A plurality of steering coil assemblies 12A and 12B, each consisting, for example, of a pair of dipolar coil units 12a and 12b as shown in FIG. 2b, are disposed along the guide tube 2 to control the orbit of the electron beam along the central axis of the guide tube 2. In particular, at the joint 2a is disposed a steering coil assembly 12A and a angle detector 15. In response to the output of the angle detector 15, the current supply to the steering coil assembly 12A is controlled by the current control device 16 to deflect the electron beam at an angle equal to that of the guide tube 2 at the joint 2a, such that the electron beam is guided along the central axis of the guide tube 2. Further, the current supply to the lower steering coil assembly 12B is controlled by the current control device 16 in response to the output of the deviation detector 5.

What is claimed is:
1. A radiotherapy device comprising:
radiation generation means for generating an electron beam;

a guide tube of a small diameter attached at one end thereof to said radiation generation means, wherein said guide tube is adapted to be inserted at another end thereof into a body of a patient, said guide tube guiding said electron beam from said radiation generation means to said body of said patient;

electron beam convergence means disposed along said guide tube, for converting said electron beam into a thin beam directed to an affected part of said body of said patient;

deviation detector means for detecting a deviation of said electron beam from a center of said guide tube; and feedback control means coupled to said deviation detector means, for controlling said electron beam convergence means to adjust an orbit of said electron beam along a central axis of said guide tube in response to an output of said deviation detector means.

2. A radiotherapy device as claimed in claim 1, wherein said electron beam convergence means includes a quadrupole magnet assembly.

3. A radiotherapy device as claimed in claim 2, wherein said electron beam convergence means further includes a steering coil assembly, disposed near said quadrupole magnet assembly, for adjusting a direction of said electron beam.

4. A radiotherapy device as claimed in claim 1, wherein said electron beam convergence means includes a quadrupole coil assembly.

5. A radiotherapy device as claimed in claim 4, wherein said electron beam convergence means further includes a steering coil assembly, disposed near said quadrupole coil assembly, for adjusting a direction of said electron beam.

6. A radiotherapy device as claimed in claim 1, further comprising:

rotation mechanism means for changing an incident angle of said electron beam into said body of said patient.

7. A radiotherapy device as claimed in claim 6, wherein said guide tube includes a joint at which said guide tube is deflectable, said electron beam convergence means including a dipolar coil assembly for deflecting said electron beam at said joint such that an orbit of said electron beam is aligned along a central axis of said guide tube.

* * * * *

UNITED STATES PATENT AND TRADEMARK OFFICE
CERTIFICATE OF CORRECTION

PATENT NO. : 5,317,164
DATED : May 31, 1994
INVENTOR(S) : Masaaki Kurokawa

It is certified that error appears in the above-indentified patent and that said Letters Patent is hereby corrected as shown below:

TITLE PAGE

<u>In the Abstract:</u> Line 7, "6" should be -- 5 --; Col. 1, lines 15-16, "60°C." should be -- $^{60}$Co --; Col. 1, line 31, "226Ra" should be -- $^{226}$Ra --; Col. 1, line 40, "60°C." should be -- $^{60}$Co --.

Signed and Sealed this

Thirteenth Day of September, 1994

Attest:

BRUCE LEHMAN

*Attesting Officer*   *Commissioner of Patents and Trademarks*